(12) United States Patent
Jeffery (10) Patent No.: US 7,876,881 B2
(45) Date of Patent: Jan. 25, 2011

(54) LINEAR ACCELERATOR WITH WIDE BORE CT SCANNER

(75) Inventor: Andrew Jeffery, Retford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 250 days.

(21) Appl. No.: 11/901,485

(22) Filed: Sep. 17, 2007

(65) Prior Publication Data
US 2009/0074134 A1    Mar. 19, 2009

(51) Int. Cl.
*A61N 5/10* (2006.01)
(52) U.S. Cl. .................. 378/65; 378/9; 378/10
(58) Field of Classification Search ........ 378/9, 378/65, 197, 10
See application file for complete search history.

(56) References Cited

U.S. PATENT DOCUMENTS

| | | | |
|---|---|---|---|
| 6,842,502 B2 * | 1/2005 | Jaffray et al. | 378/65 |
| 6,888,919 B2 | 5/2005 | Graf | |
| 7,014,361 B1 * | 3/2006 | Ein-Gal | 378/197 |
| 7,130,372 B2 | 10/2006 | Kusch et al. | |
| 7,227,925 B1 | 6/2007 | Mansfield et al. | |
| 2003/0048868 A1 | 3/2003 | Bailey et al. | |
| 2005/0226364 A1 | 10/2005 | Bernard De Man et al. | |
| 2007/0003004 A1 * | 1/2007 | Delgado et al. | 378/10 |
| 2007/0133752 A1 | 6/2007 | Ein-Gal | |
| 2008/0212859 A1 * | 9/2008 | Da Silva et al. | 378/20 |

OTHER PUBLICATIONS

PCT International Search Report dated Dec. 15, 2008 (International application No. PCT/US2008/008927).
PCT—Written Opinion of the International Searching Authority, Dec. 15, 2008, 6 pages (for International application No. PCT/US2008/008927).

* cited by examiner

Primary Examiner—Chih-Cheng G Kao (57) ABSTRACT

A system according to some embodiments may include a treatment head to emit a megavoltage radiation beam toward a volume, a plurality of X-ray sources to emit a respective kilovoltage radiation beam toward the volume while the plurality of X-ray sources are substantially stationary with respect to the volume, a detector to receive the plurality of kilovoltage radiation beams after having passed through the volume, and a processor to generate a three-dimensional image of the volume based only on the plurality of kilovoltage radiation beams received by the detector while the plurality of X-ray sources were substantially stationary with respect to the volume.

23 Claims, 9 Drawing Sheets

LINEAR ACCELERATOR WITH WIDE BORE CT SCANNER

BACKGROUND

1. Field

The embodiments described below relate generally to radiation treatment, and more particularly to imaging systems used in conjunction with such treatment.

2. Description

According to conventional radiation treatment, a beam of treatment radiation is directed toward a tumor located within a patient. The radiation beam delivers a predetermined dose of therapeutic radiation to the tumor according to an established treatment plan. The delivered radiation kills cells of the tumor by causing ionizations within the cells.

Treatment plans are therefore designed to maximize radiation delivered to a target while minimizing radiation delivered to healthy tissue. However, a treatment plan is designed assuming that relevant portions of a patient will be in a particular position relative to a treatment device during treatment. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

Due to the foregoing, treatment plans are designed under the assumption that positioning errors may occur that may result in misdelivery of radiation. Treatment plans compensate for this potential misdelivery by specifying lower doses or smaller beam shapes (e.g., beams that do not radiate edges of a tumor) than would be specified if misdelivery was not expected. Such compensation may decrease as margins of error in patient positioning decrease.

It would therefore be beneficial to provide a system and method that may increase the accuracy of patient positioning during radiation treatment. When used in conjunction with conventionally-designed treatments, more accurate positioning may reduce chances of harming healthy tissue. More accurate patient positioning may also allow the use of more aggressive treatments. Specifically, if a margin of error in patient positioning is known to be small, treatment may be designed to safely radiate a greater portion of a tumor with higher doses than in scenarios where the margin of error is larger.

SUMMARY

To address at least the above problems, some embodiments provide a system, method, medium, apparatus, and means to emit a megavoltage radiation beam from a treatment head toward a volume, emit a respective kilovoltage radiation beam from each of a plurality of X-ray sources toward the volume while the plurality of X-ray sources are substantially stationary with respect to the volume, receive the plurality of kilovoltage radiation beams at a detector after having passed through the volume, and generate a three-dimensional image of the volume based only on the plurality of kilovoltage radiation beams received by the detector while the plurality of X-ray sources were substantially stationary with respect to the volume. According to some embodiments, emission of the megavoltage radiation beam, emission of the respective kilovoltage radiation beam from each of the plurality of X-ray sources, and reception of the plurality of kilovoltage radiation beams occur simultaneously during a period at which the treatment head, the plurality of X-ray sources, and the detector are stationary.

According to some embodiments, provided are an apparatus including a treatment head to emit a megavoltage radiation beam toward a volume, a plurality of X-ray sources, each of the plurality of X-ray sources to emit a respective kilovoltage radiation beam toward the volume while the plurality of X-ray sources are substantially stationary with respect to the volume, a detector to receive the plurality of kilovoltage radiation beams after having passed through the volume, and a processor to generate a three-dimensional image of the volume based only on the plurality of kilovoltage radiation beams received by the detector while the plurality of X-ray sources were substantially stationary with respect to the volume.

In further aspects, a rotatable gantry is coupled to the treatment head and a housing houses the plurality of X-ray sources and the detector, wherein the housing is coupled to the gantry for rotation therewith. The housing may define an opening through which a portion of the treatment head passes when the housing is moved to a deployed position, and the detector and the plurality of X-ray sources may be fixed with respect to the treatment head in the deployed position.

Some embodiments provide an apparatus including a rotatable gantry, a treatment head coupled to the gantry, the treatment head to emit megavoltage radiation, and a housing coupled to the gantry, the housing to house a plurality of X-ray sources and a detector, wherein the housing defines an opening to pass a portion of the treatment head. According to further aspects, a device is coupled to the housing and to the gantry to move the housing toward the gantry to a parked position and to move the housing away from the gantry to a deployed position. A portion of the treatment head passes through the opening when the housing is moved to the deployed position. In some aspects, the detector and the plurality of X-ray sources are fixed with respect to the treatment head in the deployed position.

The claims are not limited to the disclosed embodiments, however, as those skilled in the art can readily adapt the teachings herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventor for carrying out some embodiments. Various modifications, however, will remain readily apparent to those in the art.

Figure 1:
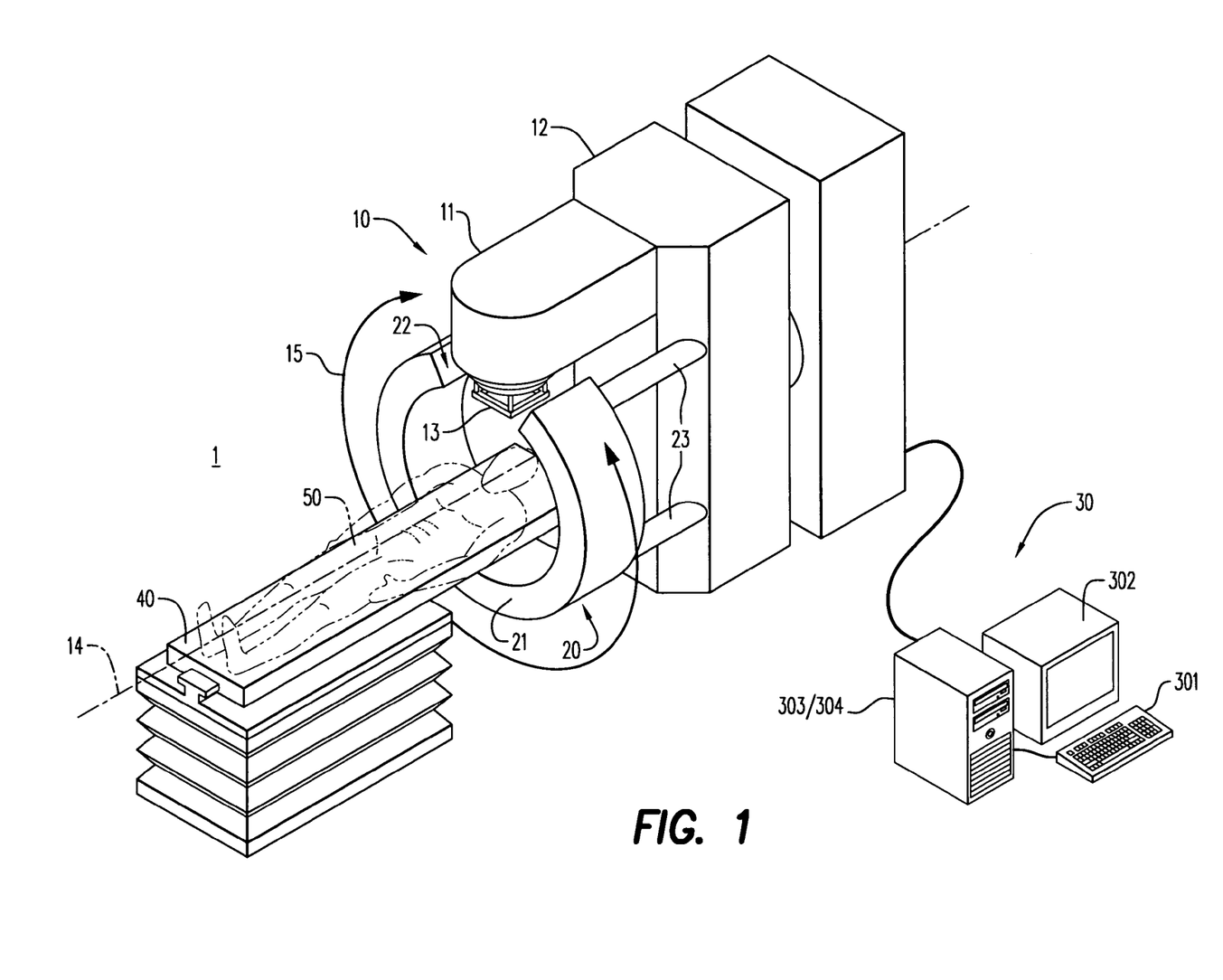
FIG. 1 is a perspective view of a radiation treatment room according to some embodiments.

FIG. 1 illustrates radiation treatment room 1 pursuant to some embodiments. Radiation treatment room 1 includes linear accelerator (linac) 10, imaging system 20, operator console 30 and table 40. The elements of radiation treatment room 1 may be used to deliver radiation treatment to a target volume of beam object 50. In this regard, beam object 50 may comprise a patient positioned to receive radiation according to a radiation treatment plan. The elements of treatment room 1 may be employed in other applications according to some embodiments.

Linac 10 generates and emits the radiation, and is primarily composed of treatment head 11 and gantry 12. Treatment head 11 includes a beam-emitting device (not shown) for emitting a radiation beam used during calibration, verification, and/or treatment. The radiation beam may comprise electron, photon or any other type of radiation. According to some embodiments, the treatment radiation comprises megavoltage radiation. Also included within treatment head 11 is a beam-shielding device, or collimator (not shown) for shaping the beam and for shielding sensitive surfaces from the beam.

Accessory tray 13 may be mounted on treatment head 11 and may be configured to receive and securely hold attachments used during the course of treatment planning and treatment. These attachments may include reticles, wedges, or the like for further defining field sizes and intensities.

Treatment head 11 is coupled to a projection of gantry 12. Gantry 12 is rotatable around gantry axis 14 before, during and after radiation treatment. Although clockwise rotation is indicated by arrow 15, gantry 12 may also or alternatively rotate counter-clockwise according to some embodiments. Rotation of gantry 12 serves to rotate treatment head 11 around axis 14.

During radiation treatment, treatment radiation is delivered from linac 10 to the beam-emitting device of treatment head 11 and is emitted therefrom as a divergent beam. The beam is emitted towards an isocenter of linac 10. The isocenter is located at the intersection of an axis of the beam and gantry axis 14. Due to divergence of the radiation beam and the shaping of the beam by the aforementioned beam-shaping devices, the beam may deliver radiation to a volume of beam object 50 rather than only to the isocenter.

Table 40 supports beam object 50 during radiation treatment. Table 40 may be adjustable to assist in positioning a treatment area of beam object 50 at the isocenter of linac 10. Table 40 may also be used to support devices used for calibration and/or verification.

Imaging system 20 may be used to acquire images that may be used before, during and/or after radiation treatment. For example, imaging system 20 may be used to acquire images for verification and recordation of a target volume position and of an internal patient portal to which radiation is delivered. As will be described in detail below, imaging device 20 may provide three-dimensional images of a target volume during emission of a megavoltage radiation beam from treatment head 11. The three-dimensional images may be used to determine whether or not radiation treatment (i.e., emission of the radiation beam) should continue. Images acquired by imaging device 20 may be used to provide four-dimensional fluoroscopy of radiation treatment according to some embodiments.

Imaging system 20 comprises housing 21 including a plurality of x-ray sources (not shown) and a detector (not shown). Each of the plurality of X-ray sources may emit a respective kilovoltage radiation beam toward the target volume while the plurality of X-ray sources are substantially stationary with respect to the volume, and the detector is to receive the plurality of kilovoltage radiation beams after having passed through the target volume. In some embodiments, a three-dimensional image of the volume may be generated based on the plurality of kilovoltage radiation beams received by the detector. Due to the foregoing arrangement, the three-dimensional image may be generated based only on the plurality of kilovoltage radiation beams received by the detector while the plurality of X-ray sources were substantially stationary with respect to the volume. Some embodiments of housing 21 including a plurality of x-ray sources and a detector will be described in detail below.

Housing 21 defines opening 22 to pass a portion of treatment head 11. Opening 22 is 1100 to 1150 mm wide in some embodiments. Opening 22 may allow an interior diameter of imaging device 20 to be larger than would be possible in the absence of opening 22. According to some embodiments, housing 21 includes several fixed components, which may also allow for a larger interior diameter because other imaging elements may be located exterior to housing 21. The larger interior diameter may more easily accommodate a body within imaging device 20 and/or may provide greater field of view of the body using the above-mentioned detector and plurality of X-ray sources.

Telescopic arms 23 are coupled to gantry 12 and to housing 21. Telescopic arms 23 may be actuated in order to move housing 21 away from gantry 12 to a deployed position as illustrated in FIG. 1. A portion of treatment head 11 passes through opening 22 when housing 21 is moved to the deployed position. Telescopic arms 23 may also move housing 21 toward gantry 12 to a parked position. Embodiments are not limited to telescopic arms 23; any suitable system that is or becomes known may be employed to move housing 21 as described.

Imaging device 20 is rotationally fixed with respect to treatment head 11 when in the deployed position. Specifically, imaging device 20 rotates along with treatment head 11 in response to any rotation of gantry 12. In some embodiments, the plurality of x-ray sources and the detector of imaging device 20 also remain fixed with respect to treatment head 11 before, during and after any rotation of gantry 12 while in the deployed position.

Figure 2:
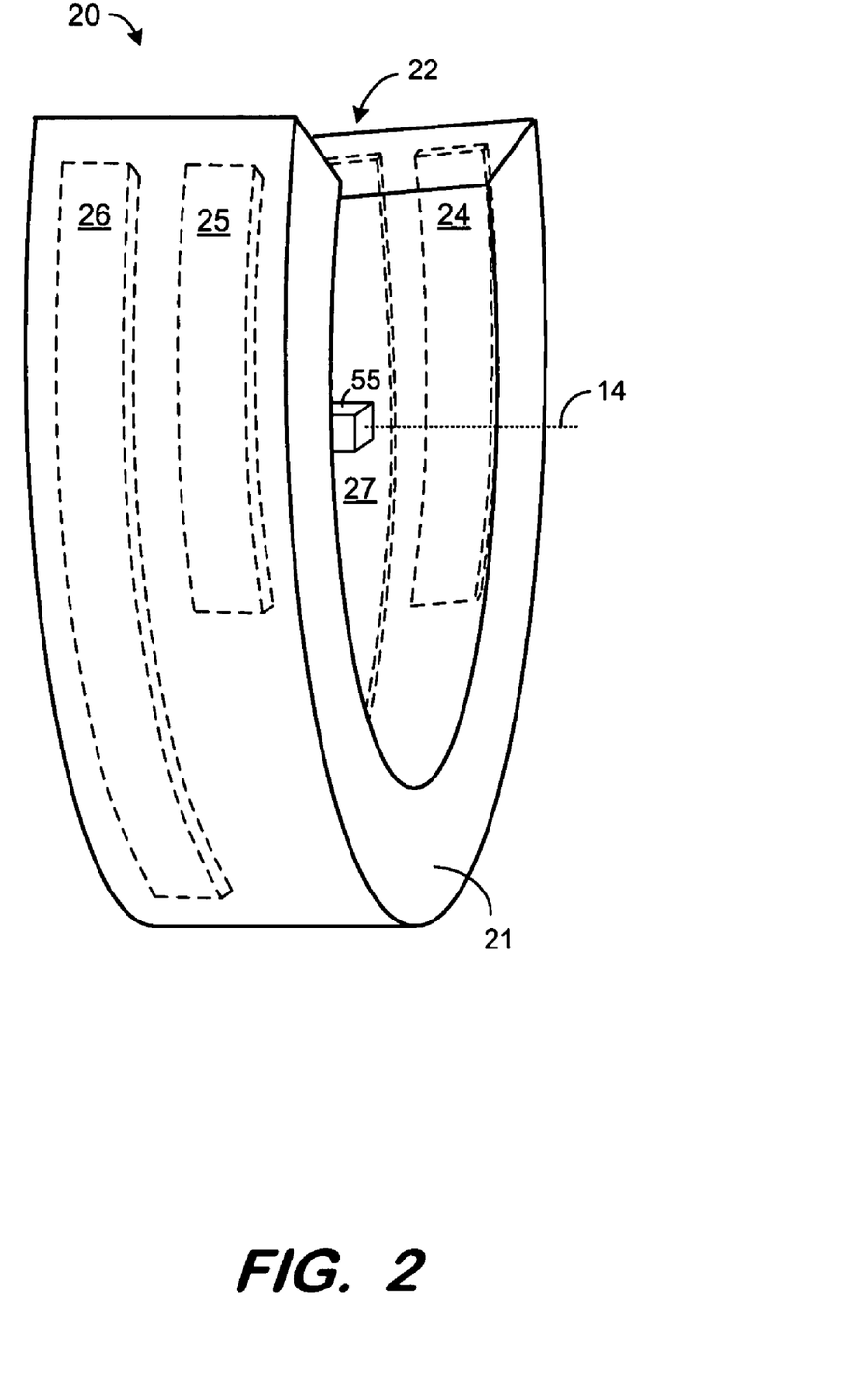
FIG. 2 is a transparent perspective view of an imaging device according to some embodiments.
Figure 3:
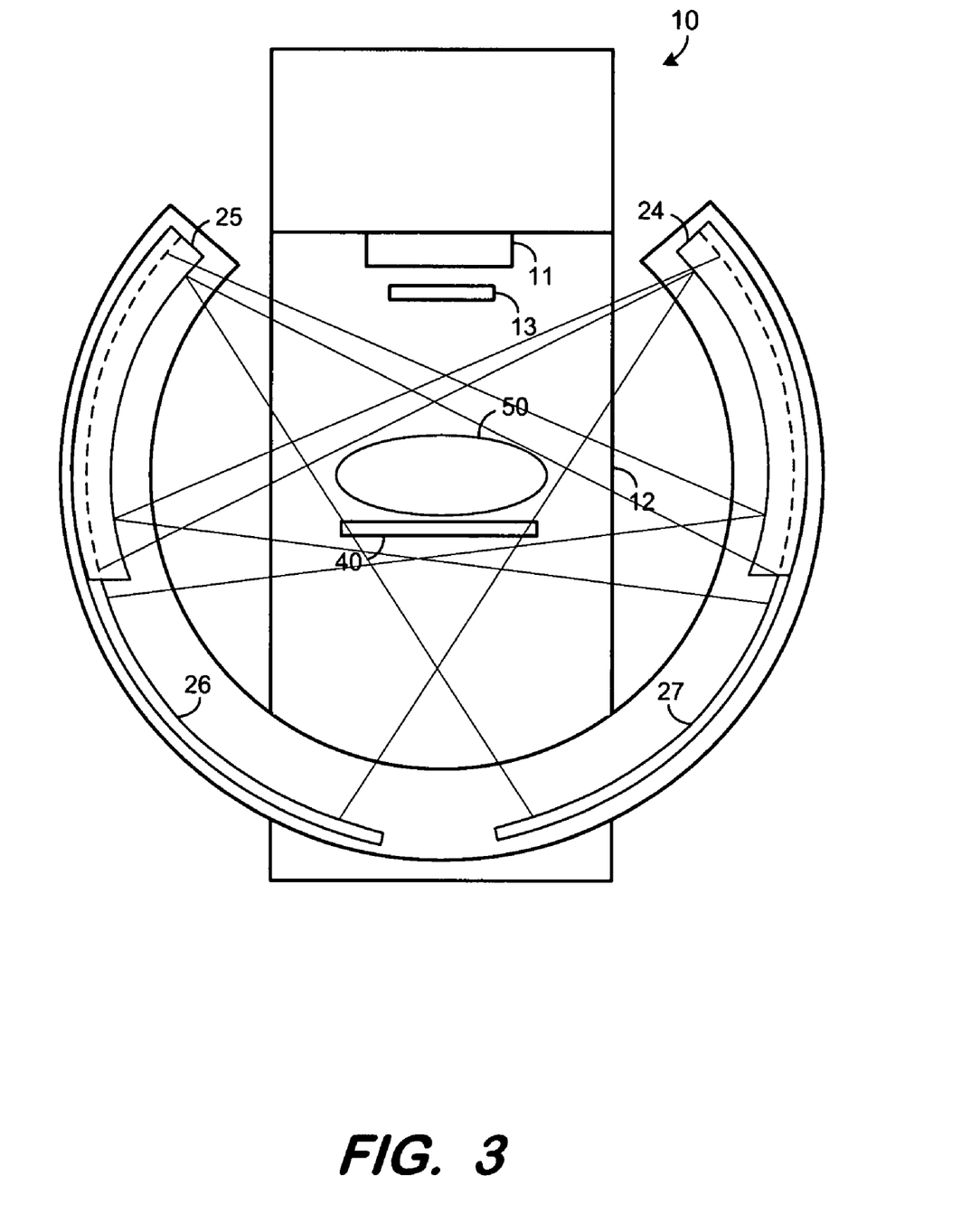
FIG. 3 is a transparent perspective view of an imaging device in a radiation treatment room according to some embodiments.

FIGS. 2 and 3 comprise transparent perspective views of imaging device 20 according to some embodiments. Imaging device 20 of FIGS. 2 and 3 comprises first plurality of X-ray sources 24, second plurality of X-ray sources 25, first detector 26 and second detector 27. As illustrated in FIG. 3, each X-ray source of X-ray sources 24 emits a kilovoltage radiation beam that passes through volume 55 and is received by first detector 26 after having passed through volume 55. Similarly, each X-ray source of X-ray sources 25 emits a kilovoltage radiation beam that passes through volume 55 and is received by second detector 27 after having passed through volume 55. In some embodiments, portions of the emitted kilovoltage radiation beams may be received by a detector without having passed through volume 55 or object 50.

First plurality of X-ray sources 24 and second plurality of X-ray sources 25 are disposed farther away from gantry 12 than detectors 26 and 27. Accordingly, X-ray sources 24 and 25 may be pointed slightly back toward gantry 12 in order for their emitted beams to fall substantially squarely on respective detectors 26 and 27.

According to some embodiments, first plurality of X-ray sources 24 and second plurality of X-ray sources 25 are disposed along a 270 degree arc surrounding volume 55. Sources 24 and 25 may be evenly spaced along the arc and may be located within a plane perpendicular to axis 14. Sources 24 and 25 may exhibit any suitable spatial configuration that is or becomes known.

Detectors 26 and 27 may acquire image data based on received radiation in any manner that is or becomes known. For example, one or both of detectors 26 and 27 may comprise a scintillator layer and solid-state amorphous silicon photodiodes deployed in a two-dimensional array. In operation, the scintillator layer receives X-rays and generates light in proportion to the intensity of the received X-rays. The array of photodiodes receives the light and records the intensity of received light as stored electrical charge. The stored charge therefore comprises an acquired image that represents intensities at each location of a radiation field produced by a radiation beam.

Detectors 26 and 27 may comprise other types of imaging devices. For example, X-ray radiation may also be converted to and stored as electrical charge without use of a scintillator layer. In such imaging devices, X-rays are absorbed directly by an array of amorphous selenium photoconductors. The photoconductors convert the x-rays directly to stored electrical charge that comprises an acquired image of a radiation field. Detectors 26 and 27 may also comprise a CCD or tube-based camera. Such an imaging device may include a light-proof housing within which are disposed a scintillator, a mirror, and a camera.

The electrical charge acquired by detectors 26 and 27 represents attenuative properties of tissues through which the received radiation beams have passed. More specifically, each X-ray source of housing 21 creates a projection image by emitting a radiation beam toward its respective detector, and each projection image represents attenuative properties of tissues through which its respective beam has passed. Due to the arrangement of X-ray sources within housing 21, the projection images may overlap as illustrated in FIG. 3. Known computed tomography-based techniques may be used to generate a three-dimensional image based on the overlapping projection images. Such techniques may also take into account the different orbits around volume 55 within which X-ray sources 24 and 25 and detectors 26 and 27 reside.

Some embodiments of the foregoing features enable generation of a three-dimensional image based only on radiation beams emitted from sources 24 and 25 while in a substantially stationary position with respect to volume 55. In contrast, other systems require the rotation of X-ray sources around a target volume to successively acquire the projection images that are required to generate a three-dimensional image.

Figure 4:
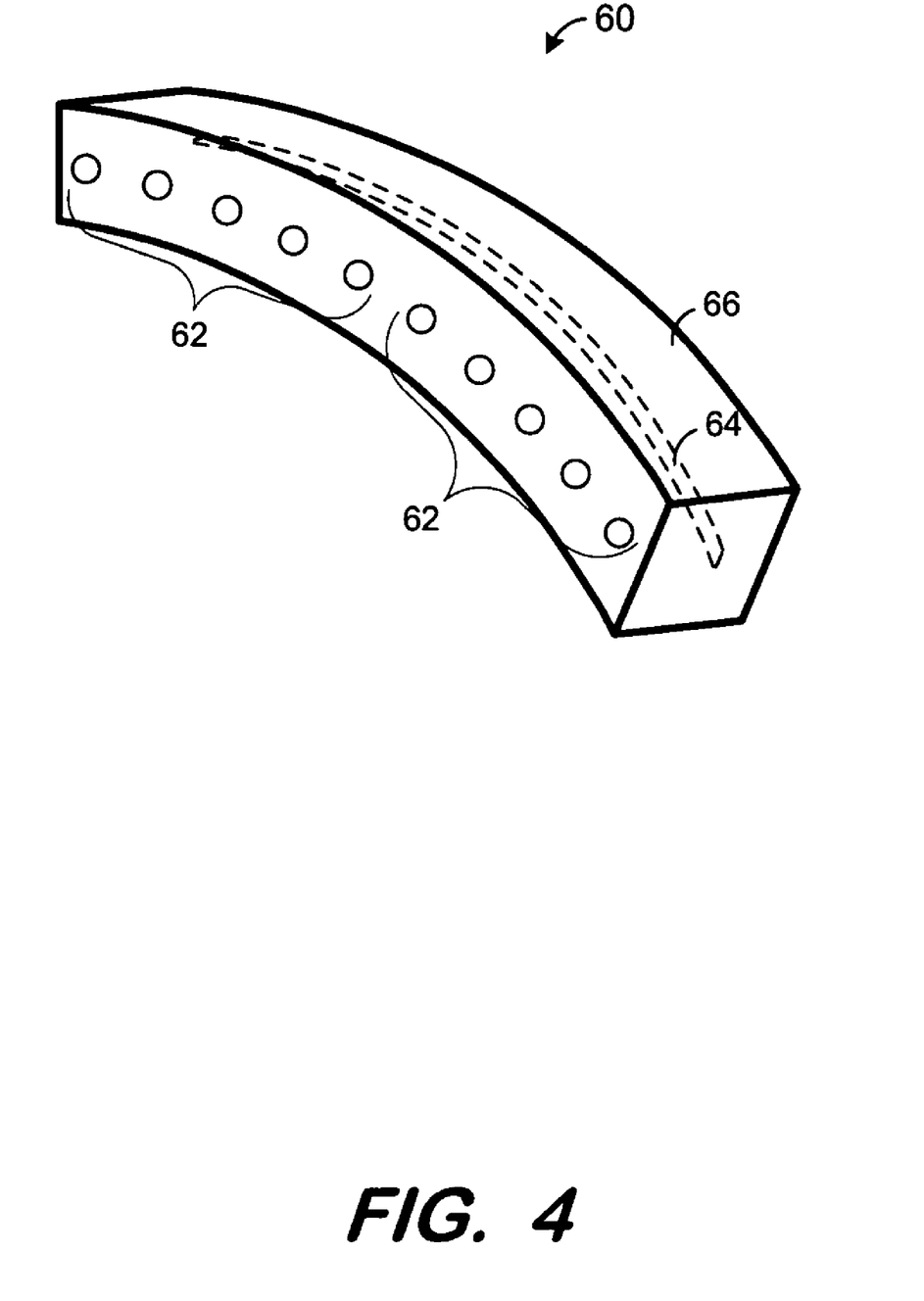
FIG. 4 is a perspective view of a plurality of radiation sources according to some embodiments.

FIG. 4 is a perspective view of plurality of X-ray sources 60 according to some embodiments. X-ray sources 60 comprise a plurality of cathodes 62 associated with single long anode 64. Anode 64 and cathodes 62 may be cooled by recirculating oil within enclosure 66 according to some embodiments. In some embodiments, first plurality of X-ray sources 24 and second plurality of X-ray sources 25 each consist of two sources 60 of FIG. 4. The plurality of X-ray sources used in some embodiments may comprise any suitable device or devices to emit kilovoltage radiation that are or become known, including but not limited to discrete X-ray tubes.

Returning to FIG. 1, operator console 30 includes input device 301 for receiving instructions from an operator and output device 302, which may be a monitor for presenting operational parameters of linac 10 and imaging device 20 and/or interfaces for receiving instructions. Such instructions may include an instruction to move imaging device 20 from a parked position to the deployed position illustrated in FIG. 1, an instruction to emit kilovotage radiation beams from a plurality of X-ray sources of device 20, or an instruction to generate a three-dimensional image of object 50 based on the emitted radiation beams. Output device 302 may also present such a three-dimensional image and/or two-dimensional "slice" images based on the three-dimensional image.

Input device 301 and output device 302 are coupled to processor 303 and storage 304. Processor 303 may execute program code to cause imaging device to perform any of the above-mentioned steps, and to generate three-dimensional images and slice images based on kilovoltage radiation beams received by a detector of device 20. The program code, three-dimensional images and slice images may be stored in storage 304.

Storage 304 may also store program code to generate and/or modify a treatment plan according to some embodiments. Such code may comprise the COHERENCE™ workspace or the KONRAD™ treatment planning system sold by Siemens Medical Solutions. Accordingly, storage 304 may also store radiation treatment plans in accordance with any currently- or hereafter-known format. The treatment plans may comprise scripts that are automatically executable by elements of room 1 to provide radiation therapy fractions. Each treatment plan may require a patient to be positioned in a particular manner with respect to treatment head 11.

Operator console 30 may be in a room other than treatment room 1, in order to protect its operator from radiation. For example, treatment room 1 may be heavily shielded, such as a concrete vault, to shield the operator from radiation generated by linac 10.

Each of the devices shown in FIGS. 1 through 4 may include less or more elements than those shown. In addition, embodiments are not limited to the devices shown in FIGS. 1 through 4.

Figure 5:
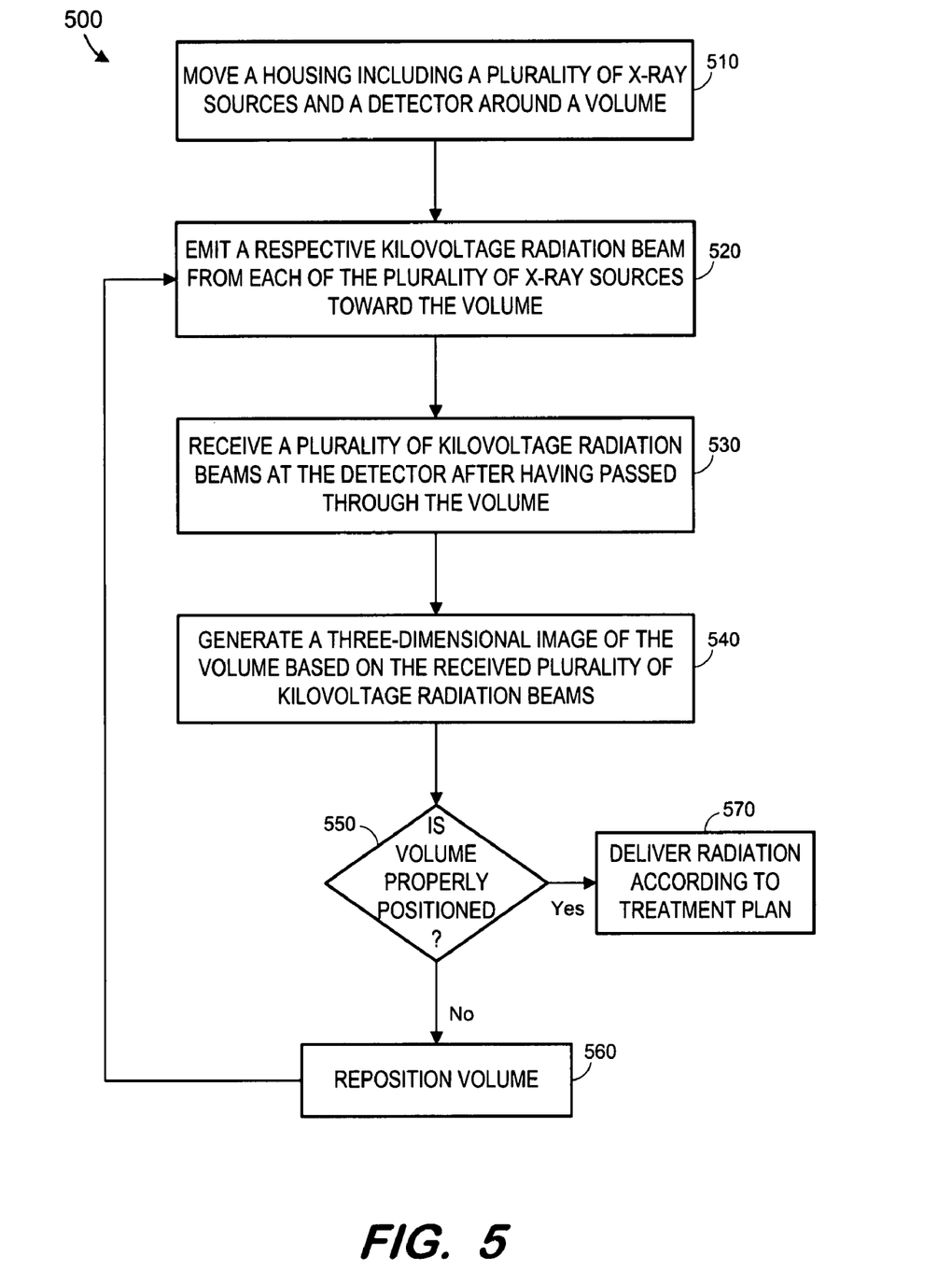
FIG. 5 is a flow diagram of process steps according to some embodiments.

FIG. 5 is a flow diagram of a process according to some embodiments. Process 500 may be performed using any suitable combination of hardware, software or manual means. Examples of process 500 will be described below with respect to the elements of treatment room 1, but embodiments are not limited thereto.

Figure 6:
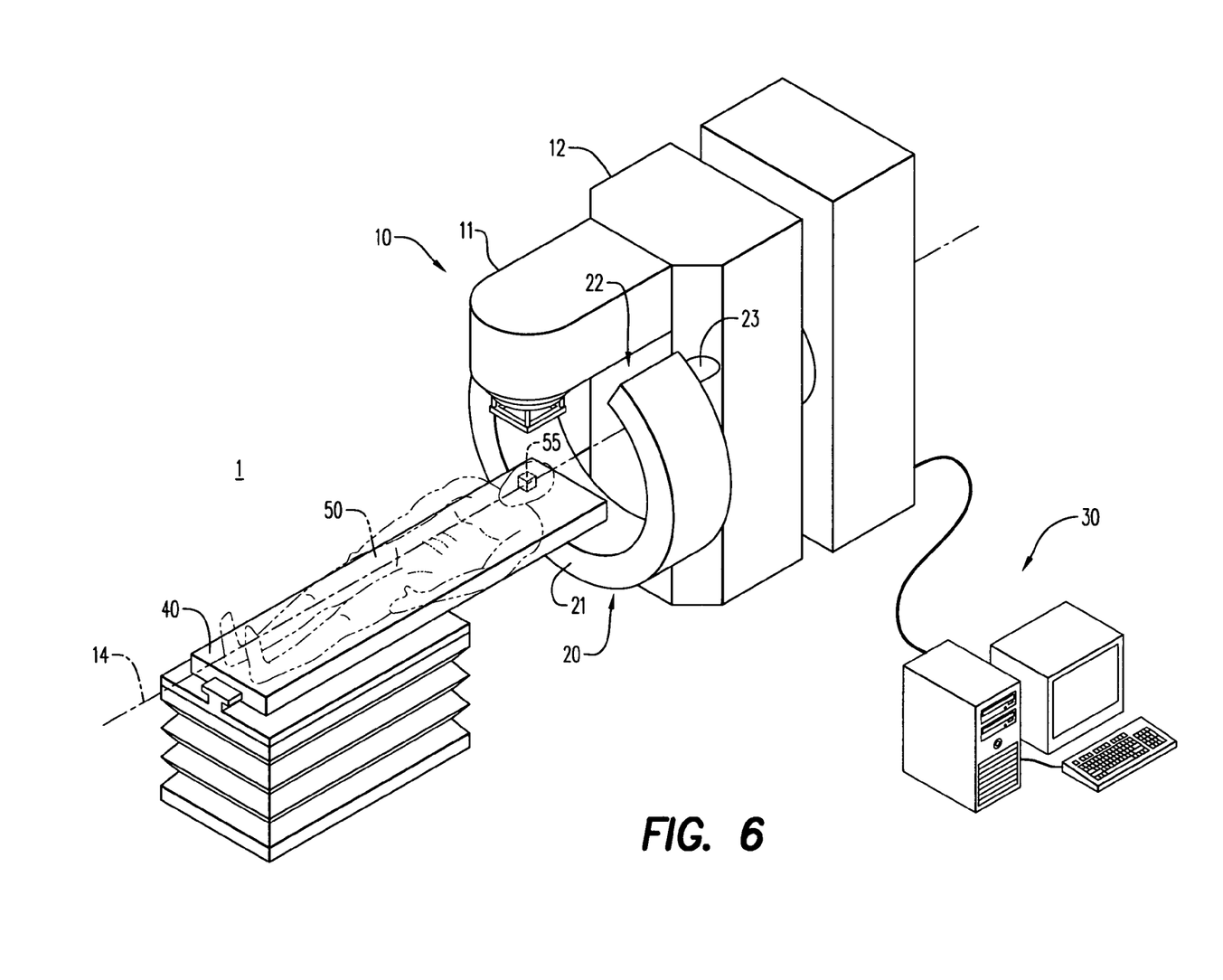
FIG. 6 is a perspective view of a radiation treatment room with an imaging device in a parked position according to some embodiments.

Initially, at 510, a housing including a plurality of X-ray sources and a detector is moved around a volume. FIG. 6 illustrates treatment room 1 prior to 510 according to some embodiments. As shown, beam object 50 is disposed on table 40 such that target volume 55 is located at an isocenter of linac 10. Imaging device 20, including a plurality of X-ray sources and a detector, is located in a "parked" position adjacent to gantry 12. The parked position is typically unsuitable for generating images of target volume 55, and may be utilized when no imaging is required.

Telescopic arms 23 may move housing 21 from the parked position to the deployed position of FIG. 1 at 510. According to some embodiments of 510, linac 10 receives an instruction from operator console 30 to actuate telescopic arms 23. As described above, a portion of treatment head 11 passes through opening 22 of housing 21 when housing 21 is moved from the parked position to the deployed position.

A respective kilovoltage radiation beam is emitted from each of the plurality of X-ray sources toward the volume at 520. In some embodiments, operator console 30 controls imaging device 20 to emit a kilovoltage radiation beam from each of radiation sources 24 and 25 toward target volume 55. Radiation sources 24 and 25 may be substantially stationary with respect to target volume 55 during 520. Consequently, a plurality of kilovoltage radiation beams is received at the detector at 530 after having passed through the volume. FIGS. 2 and 3 illustrate some embodiments of 530 in which first detector 26 and second detector 27 each receive a plurality of kilovoltage radiation beams that has passed through volume 55.

A three-dimensional image is generated at 540 based only on the plurality of kilovoltage radiation beams received while the X-ray sources were substantially stationary. Detectors 26 and 27, for example, generate a projection image corresponding to each received radiation beam. Operator console 30 or any other element of treatment room 10 may apply currently- or hereafter-known computed tomography-based techniques to generate a three-dimensional image based on the projection images. As mentioned above, these techniques may take into account the different orbits around volume 55 within which X-ray sources 24 and 25 and detectors 26 and 27 reside.

At 550, it is determined whether the volume is properly positioned for radiation treatment. The determination at 550 may comprise comparing the generated three-dimensional image with an image provided by a pre-defined radiation treatment plan. In this regard, slice images generated from the three-dimensional image may be compared with slice images associated with the radiation treatment plan. According to some embodiments of 550, spatial coordinates of target volume 55 may be determined based on the generated three-dimensional image and compared with stored spatial coordinates.

The volume is repositioned at 560 if it is determined at 550 that the target volume is not properly positioned. The repositioning may be performed based on position error information output at 550. For example, the determination at 550 may comprise determining a specific translational and/or rotational spatial error (e.g., 4 mm X-axis, 0 mm Y-axis, −3 mm Z-axis) and the volume may be repositioned at 560 based on the determined error. Flow returns to 520 and proceeds as described above after 560.

Radiation is delivered according to a treatment plan at 570 if the determination at 550 is affirmative. More specifically, operator console 30 may control linac 10 at 570 to emit a megavoltage radiation beam toward target volume 55. The radiation beam may exhibit an energy, a shape, and a dose rate specified by a radiation treatment plan. According to some embodiments, 570 comprises rotating gantry 12 to various rotational positions and delivering a radiation beam to target volume 55 from each of the various positions. Imaging device 20 may be disposed in the deployed position or in the parked position at 570.

Figure 7:
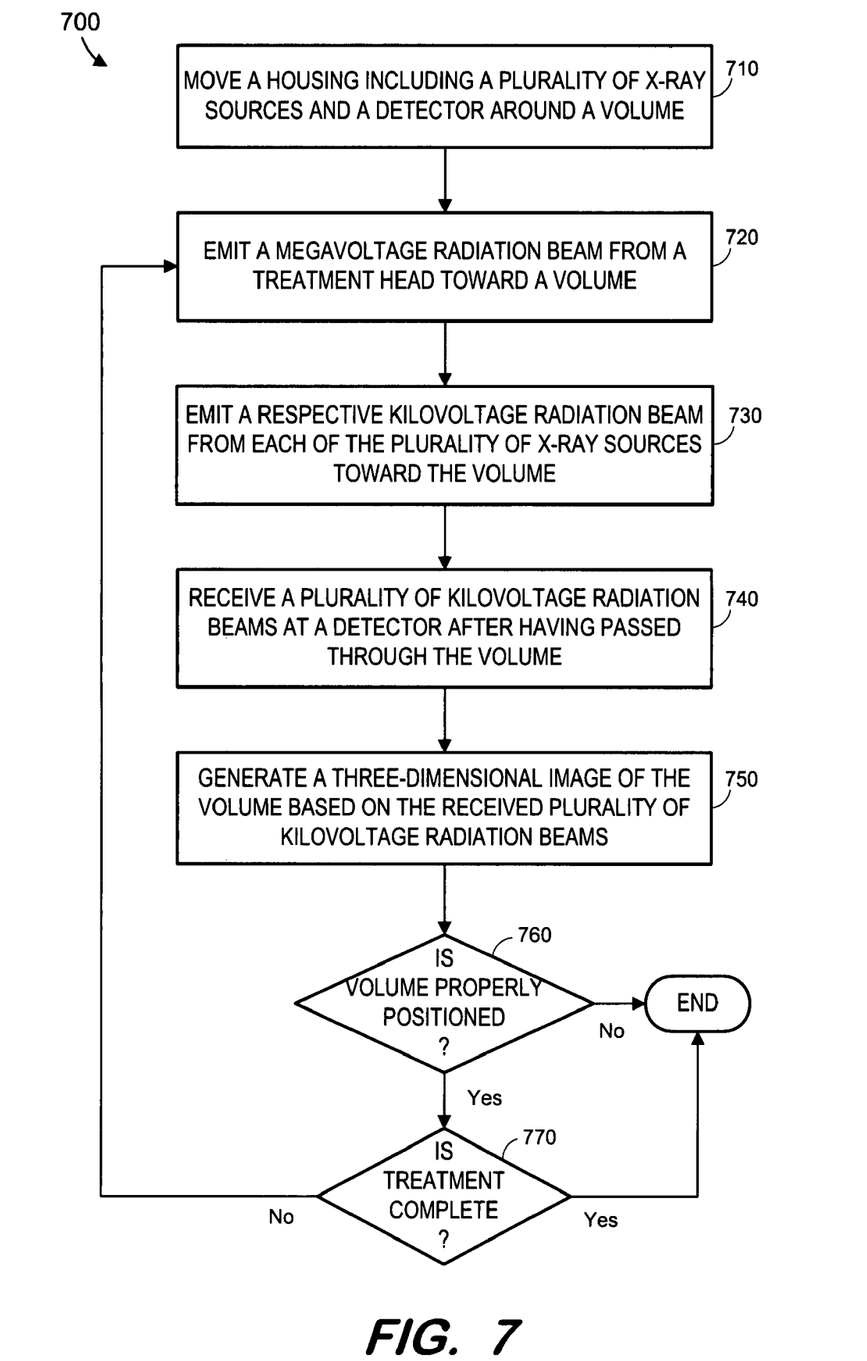
FIG. 7 is a flow diagram of process steps according to some embodiments.

FIG. 7 comprises process 700 according to some embodiments. Process 700 may be performed to confirm target volume positioning during radiation delivery. Process 700 may be performed using any suitable combination of hardware, software or manual means.

A housing including a plurality of X-ray sources and a detector is moved around a volume at 710. 710 may proceed as described above with respect to 510. In some embodiments, housing 21 is fixed in the position shown in FIG. 1, and 710 is performed during construction of linac 10.

A megavoltage radiation is emitted from a treatment head toward a volume at 720. The volume is located at an isocenter of the treatment head. In the present example, treatment head emits a megavoltage radiation beam toward volume 55 under control of operator console 30. Operator console 30, in turn, controls linac 10 and the radiation beam parameters according to a radiation treatment plan.

Figure 8:
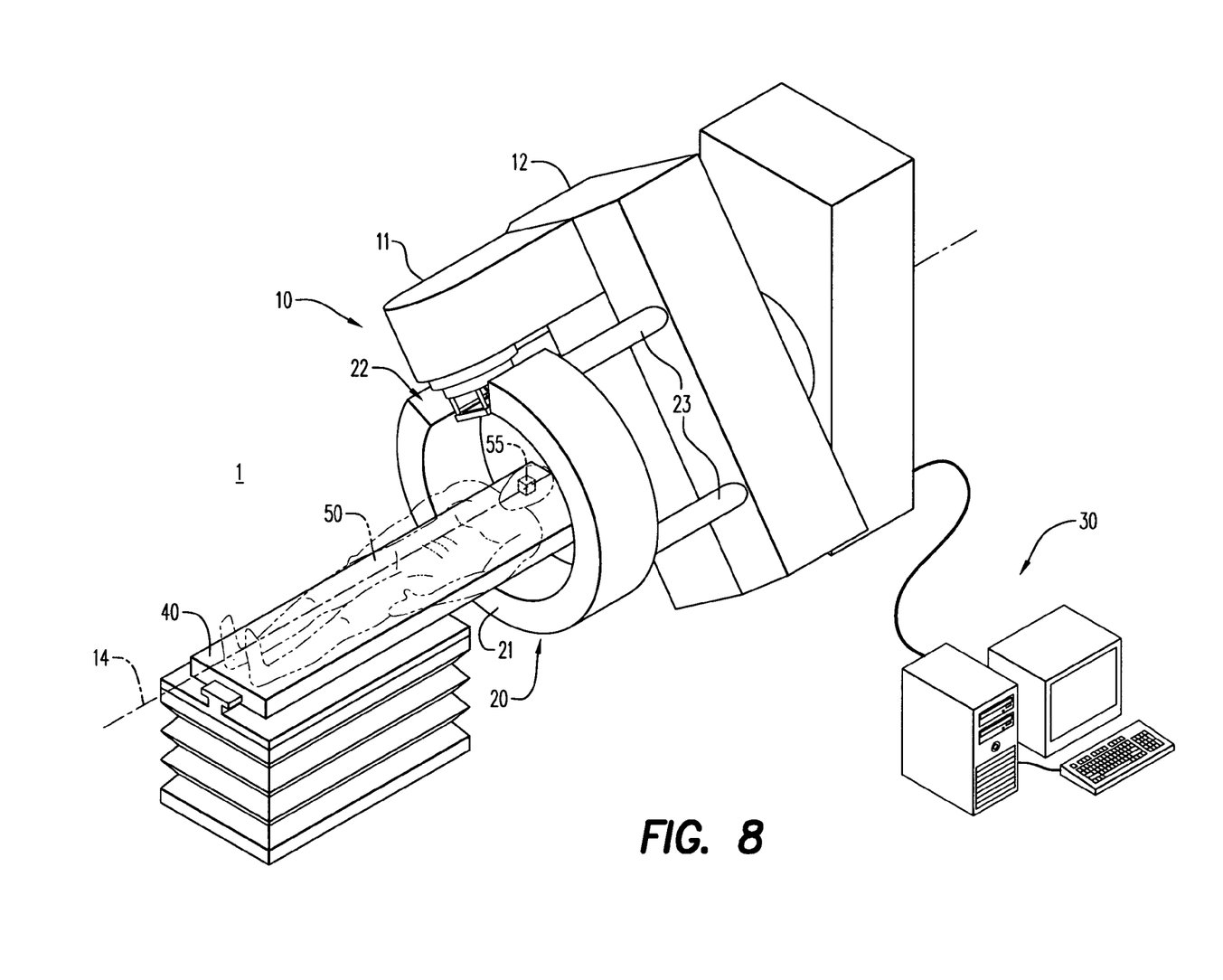
FIG. 8 is a perspective view of a radiation treatment room according to some embodiments.

In some embodiments of 720, the treatment head need not be positioned as illustrated in FIG. 1. FIG. 8 illustrates an embodiment in which gantry 12 has been rotated around axis 14. As a result, treatment head 11 and imaging device 20 have correspondingly rotated around target volume 55.

Each of the plurality of X-ray sources of the housing emits a respective kilovoltage radiation beam toward the volume at 730 while the plurality of X-ray sources are substantially stationary with respect to the volume. As mentioned above, a plurality of kilovoltage radiation beams is received at the detector at 740 after having passed through the volume. Next, at 750, a three-dimensional image is generated based on the received plurality of kilovoltage radiation beams. Some embodiments of 730, 740 and 750 have been described herein and will not be repeated for the sake of brevity.

It is then determined whether the volume is properly positioned at 760. The determination at 760 may comprise, but is not limited to, any of the positioning determinations described herein. According to some embodiments, the treatment head may continue to emit the megavoltage radiation beam during 730, 740, 750 and 760. In such embodiments, it may be possible to efficiently facilitate radiation treatment monitoring.

Figure 9:
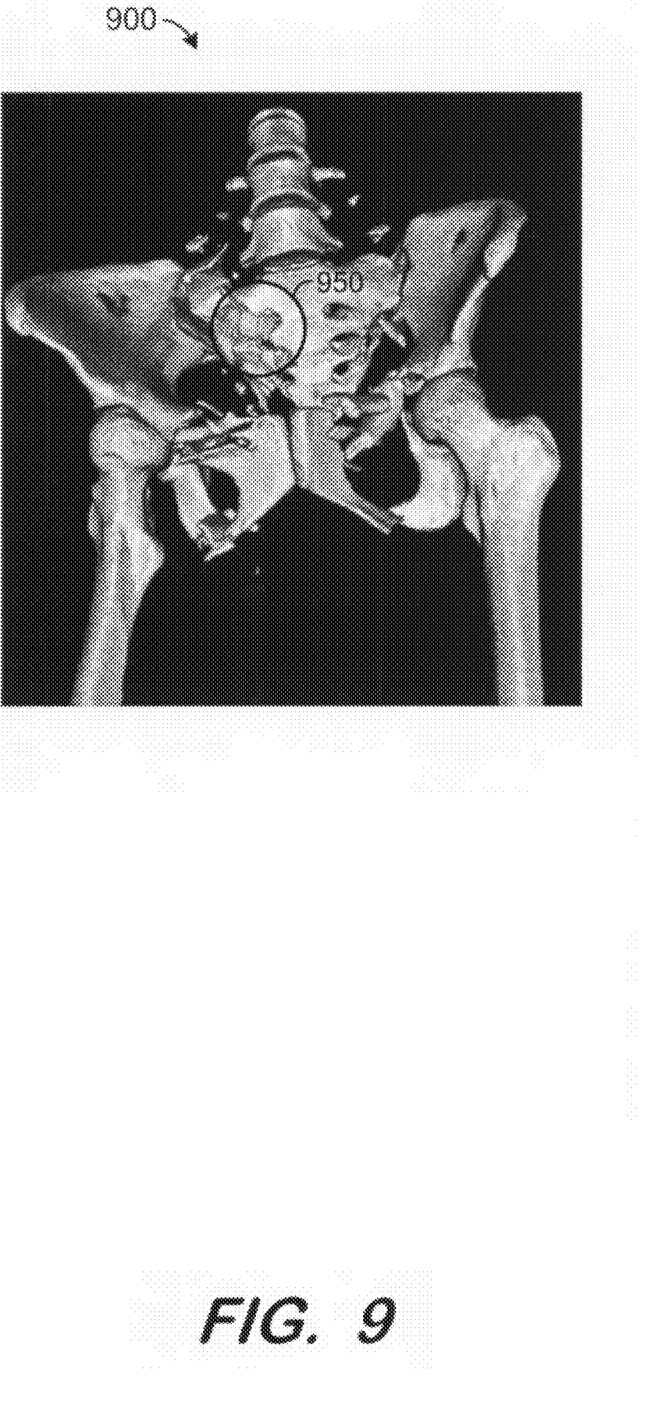
FIG. 9 is a view of a three-dimensional image showing a location of a radiation beam according to some embodiments.

FIG. 9 illustrates image 900 that may displayed on output device 302 of operator console according to some embodiments of process 700. Image 900 comprises a three-dimensional image generated at 750 and indicator 950 superimposed on the three-dimensional image. Indicator 950 of image 900 represents a position of the megavoltage radiation beam emitted from the treatment head. The position may be detected by the detector(s) and/or may be determined based on a position of gantry 12 and a known size and shape of the radiation beam. As mentioned above, the megavoltage radiation beam represented by indicator 950 may be emitted before, during or after 730, 740 and/or 750 of process 700.

Process 700 terminates after 760 if it is determined that the volume is not properly positioned. According to some embodiments, the volume may be repositioned as described above after 760 with radiation treatment resuming thereafter. Flow proceeds to 770 if it is determined that the volume is properly positioned.

Flow returns to 720 if it is determined at 770 that treatment is not complete. Flow therefore continues as described above through 720, 730, 740, 750 and 760 until treatment is complete. Imaging device 20 may be disposed in the deployed position or in the parked position during 720, 750, 760 and/or 770.

According to some embodiments, gantry 12 may be rotated and/or characteristics of the megavoltage radiation beam may be changed at any time during process 700. For example, treatment head 11 may be rotated around target volume 55 after 770 and prior to returning to 720. Process 700 may therefore be used to perform several radiation treatment fractions.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. An apparatus comprising:
    a treatment head to emit a megavoltage radiation beam toward a volume;
    a plurality of X-ray sources, each of the plurality of X-ray sources to emit a respective kilovoltage radiation beam toward the volume;
    a detector to receive a kilovoltage radiation beam from each of the plurality of X-ray sources while the plurality of X-ray sources are substantially stationary with respect to the volume; and
    a processor configured to generate a three-dimensional image of the volume based only on the plurality of kilovoltage radiation beams received by the detector while the plurality of X-ray sources were substantially stationary with respect to the volume.

2. An apparatus according to claim 1, wherein the plurality of X-ray sources circumscribe a 270 degree arc around the volume.

3. An apparatus according to claim 1, wherein the detector comprises a first detector and a second detector, and
wherein the plurality of X-ray sources comprise:
a first plurality of X-ray sources, each of the first plurality of X-ray sources to emit a respective kilovoltage radiation beam through the volume toward the first detector; and
a second plurality of X-ray sources, each of the second plurality of X-ray sources to emit a respective kilovoltage radiation beam through the volume toward the second detector.

4. An apparatus according to claim 1, wherein the plurality of X-ray sources comprise a plurality of cathodes and an associated anode.

5. An apparatus according to claim 1, further comprising:
a rotatable gantry coupled to the treatment head; and
a housing to house the plurality of X-ray sources and the detector,
wherein the housing is coupled to the gantry for rotation therewith.

6. An apparatus according to claim 5, further comprising:
a device coupled to the housing and to the gantry, the device to move the housing toward the gantry to a parked position and to move the housing away from the gantry to a deployed position.

7. An apparatus according to claim 6, wherein the housing defines an opening through which a portion of the treatment head passes when the housing is moved to the deployed position.

8. An apparatus according to claim 6, wherein the detector and the plurality of X-ray sources are fixed with respect to the treatment head in the deployed position.

9. An apparatus comprising:
a rotatable gantry;
a treatment head coupled to the gantry, the treatment head to emit megavoltage radiation; and
a housing coupled to the gantry, the housing to house a plurality of X-ray sources and a detector,
wherein the housing defines an opening to pass a portion of the treatment head, and
wherein the treatment head resides in the opening while each of the plurality of X-ray sources emits a respective kilovoltage radiation beam toward a volume, the detector receives each kilovoltage radiation beam, and a three-dimensional image of the volume is generated based only on each of the kilovoltage radiation beams received by the detector.

10. An apparatus according to claim 9, the apparatus further comprising:
a processor to generate the three-dimensional image of the volume.

11. An apparatus according to claim 9, wherein the plurality of X-ray sources circumscribe a 270 degree arc.

12. An apparatus according to claim 9, wherein the detector comprises a first detector and a second detector, and
wherein the plurality of X-ray sources comprise:
a first plurality of X-ray sources, each of the first plurality of X-ray sources to emit a respective kilovoltage radiation beam through the volume toward the first detector; and
a second plurality of X-ray sources, each of the second plurality of X-ray sources to emit a respective kilovoltage radiation beam through the volume toward the second detector.

13. An apparatus according to claim 12, wherein the plurality of X-ray sources comprise a plurality of cathodes and an associated anode.

14. An apparatus according to claim 9, further comprising:
a device coupled to the housing and to the gantry, the device to move the housing toward the gantry to a parked position and to move the housing away from the gantry to a deployed position.

15. An apparatus according to claim 14, wherein a portion of the treatment head passes through the opening when the housing is moved to the deployed position.

16. An apparatus according to claim 14, wherein the detector and the plurality of X-ray sources are fixed with respect to the treatment head in the deployed position.

17. A method comprising:
emitting a megavoltage radiation beam from a treatment head of an apparatus toward a volume;
emitting a respective kilovoltage radiation beam from each of a plurality of X-ray sources of the apparatus toward the volume while the plurality of X-ray sources are substantially stationary with respect to the volume;
receiving the plurality of kilovoltage radiation beams at a detector; and
generating a three-dimensional image of the volume based only on the plurality of kilovoltage radiation beams received by the detector while the plurality of X-ray sources were substantially stationary with respect to the volume.

18. A method according to claim 17, wherein the plurality of X-ray sources circumscribe a 270 degree arc around the volume.

19. A method according to claim 17, wherein the detector comprises a first detector and a second detector, and
wherein emitting the respective kilovoltage radiation beam from each of the plurality of X-ray sources comprises:
emitting a respective kilovoltage radiation beam from each of a first plurality of X-ray sources through the volume toward the first detector; and
emitting a respective kilovoltage radiation beam from each of a second plurality of X-ray sources through the volume toward the second detector.

20. A method according to claim 17, wherein the plurality of X-ray sources comprise a plurality of cathodes and an associated anode.

21. A method according to claim 17, further comprising:
moving the detector and the plurality of X-ray sources from a parked position to a deployed position around the volume.

22. A method according to claim 17, wherein emitting the megavoltage radiation beam, emitting the respective kilovoltage radiation beam from each of the plurality of X-ray sources, and receiving the plurality of kilovoltage radiation beams occur simultaneously during a period at which the treatment head, the plurality of X-ray sources, and the detector are stationary.

23. A method according to claim 17, further comprising:
rotating the gantry to which the treatment head, the plurality of X-ray sources, and the detector are coupled;
emitting a second megavoltage radiation beam from the treatment head toward the volume;
emitting a second respective kilovoltage radiation beam from each of the plurality of X-ray sources toward the volume while the plurality of X-ray sources are substantially stationary with respect to the volume;
receiving the second plurality of kilovoltage radiation beams at the detector after having passed through the volume; and
generating a second three-dimensional image of the volume based only on the plurality of kilovoltage radiation beams received by the detector while the plurality of X-ray sources were substantially stationary with respect to the volume.

* * * * *